United States Patent
Fasoli et al.

(10) Patent No.: US 10,441,227 B2
(45) Date of Patent: Oct. 15, 2019

(54) CEPHALOSTAT

(71) Applicant: CEFLA SOCIETÁ COOPERATIVA, Imola (IT)

(72) Inventors: Martino Fasoli, Imola (IT); Giacomo Zoccatelli, Imola (IT)

(*) Notice: Subject to any disclaimer, the term of this patent is extended or adjusted under 35 U.S.C. 154(b) by 154 days.

(21) Appl. No.: 15/491,136

(22) Filed: Apr. 19, 2017

(65) Prior Publication Data
US 2017/0303872 A1 Oct. 26, 2017

(30) Foreign Application Priority Data
Apr. 20, 2016 (IT) .................. 102016000040402

(51) Int. Cl.
| | |
|---|---|
| *A61B 6/04* | (2006.01) |
| *A61B 6/14* | (2006.01) |
| *A61B 6/00* | (2006.01) |
| *A61B 6/03* | (2006.01) |
| *A61B 90/00* | (2016.01) |

(52) U.S. Cl.
CPC ............. *A61B 6/04* (2013.01); *A61B 6/032* (2013.01); *A61B 6/0421* (2013.01); *A61B 6/0442* (2013.01); *A61B 6/14* (2013.01); *A61B 6/4085* (2013.01); *A61B 6/501* (2013.01); *A61B 6/547* (2013.01); *A61B 6/0492* (2013.01); *A61B 2090/3966* (2016.02)

(58) Field of Classification Search
CPC ... A61B 2090/3966; A61B 6/032; A61B 6/04; A61B 6/0421; A61B 6/0442; A61B 6/0492; A61B 6/14; A61B 6/4085; A61B 6/501; A61B 6/547
See application file for complete search history.

(56) References Cited

U.S. PATENT DOCUMENTS

| | | | |
|---|---|---|---|
| 6,947,038 B1 * | 9/2005 | Anh | G06T 17/10 345/419 |
| 2013/0114799 A1 | 5/2013 | Yamakawa | |
| 2015/0297152 A1 * | 10/2015 | Bianconi | A61B 6/04 378/208 |
| 2015/0374320 A1 | 12/2015 | Suuronen | |

FOREIGN PATENT DOCUMENTS

| | | |
|---|---|---|
| EP | 0534548 | 3/1993 |
| EP | 2942014 | 11/2015 |

* cited by examiner

*Primary Examiner* — Mark R Gaworecki
(74) *Attorney, Agent, or Firm* — Themis Law

(57) ABSTRACT

A cephalostat for acquiring teleradiographic images through an extraoral radiographic apparatus includes a pair of earpieces at the ends of two shafts and a small bar for resting again the nasion, these components being manually adjustable to adjust them to the skull of the patient under examination, wherein the cephalostat is free from metallic elements in the parts on which X-rays impinge, with the exception of radio-opaque markers, and is interchangeable with a craniostat fixed in the same apparatus seat.

10 Claims, 9 Drawing Sheets

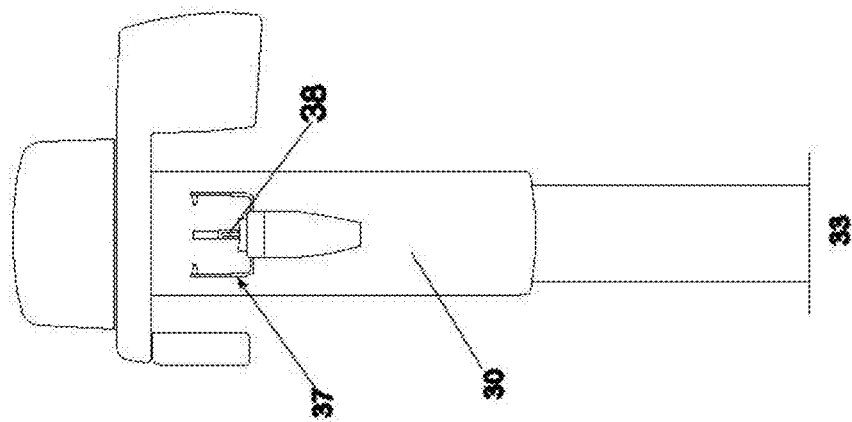
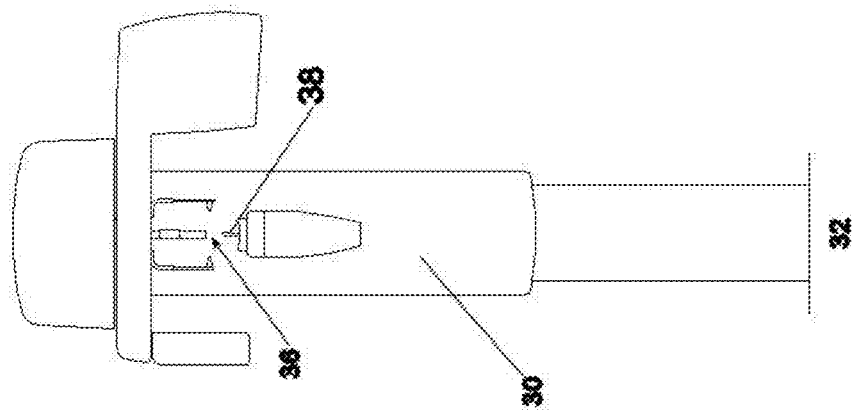
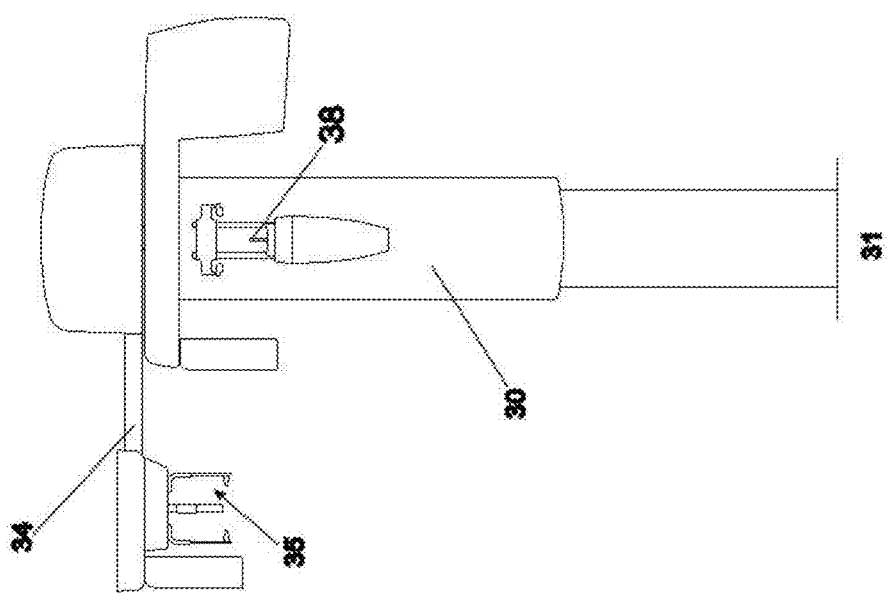
PRIOR ART
Fig. 3a
Fig. 3b
Fig. 3c

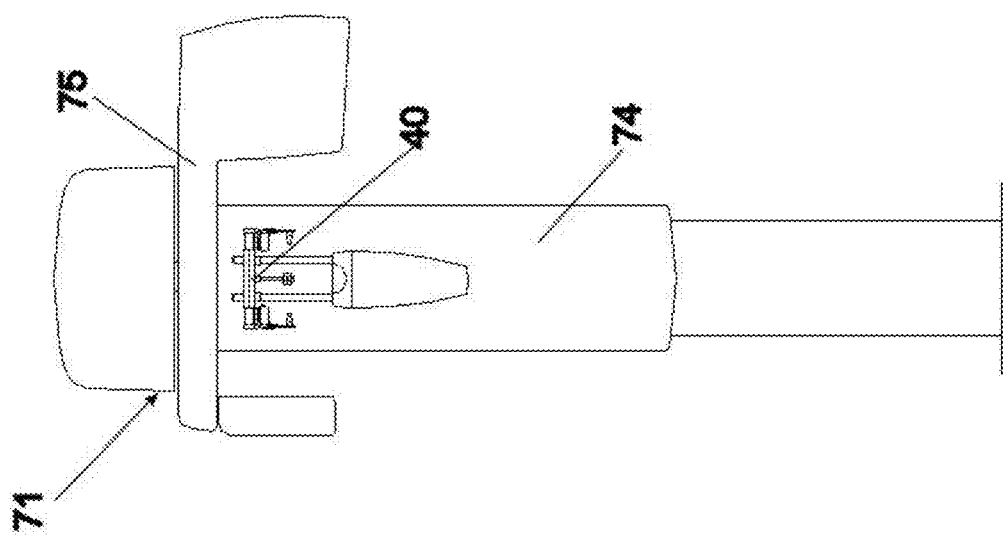
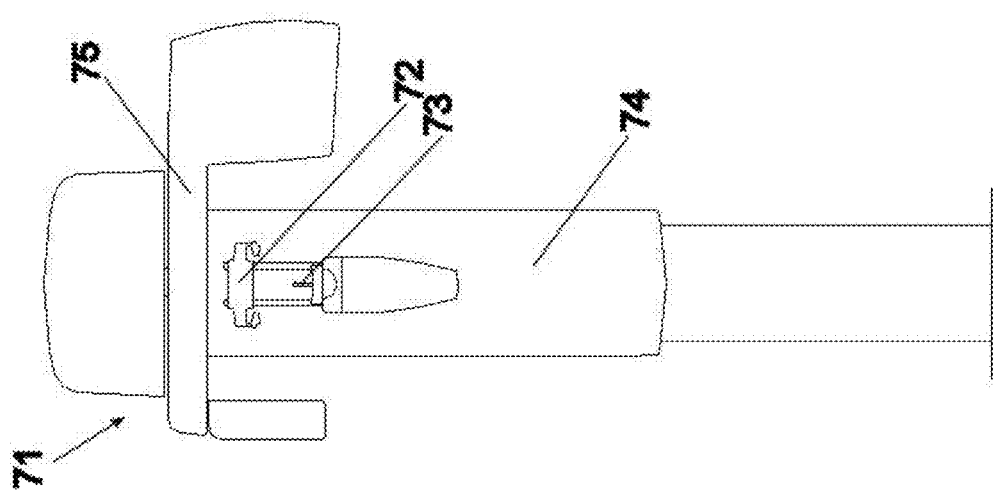

CEPHALOSTAT

FIELD OF THE INVENTION

The present invention relates to a cephalostat to be used with extraoral radiographic apparatuses for dental applications, having an X-ray source and detector capable of performing volumetric or planar scans of patient facial bones.

BACKGROUND OF THE INVENTION

Generally, extraoral radiographic apparatuses have a similar structure: a rotating C-arm, supporting at one of its ends an X-ray source and at the other end an X-ray detector; the C-arm rotates about patient's head. The X-ray source generates an X-ray bundle, which is detected by the detector and processed by a computer, so allowing the reconstruction of two-dimensional (2D) or volumetric (3D) radiographic images. Said C-arm is supported by a column, which can vary its position in height in order to adjust it according to patient's stature.

In dentistry, different kinds of radiographic image are known: hereunder a brief description of different types of acquisitions is offered, to which reference will be made in the following.

Panoramic radiography (also known as orthopantomography, abbreviated as PAN) produces a radiographic image of a curved plan approximating patient jaws, with blurring of the anatomical structures laying outside a narrow layer around the predesigned curved plane. It is a planar radiography, to which reference will be made in the following as 2D, too.

Cone beam volumetric radiography (also known as CBCT or 3D) is the acquisition, from different projection angles, of a series of two-dimensional radiographic images, which will be processed column-acquisition to reconstruct three-dimensional volumes.

Teleradiography (abbreviated as CEPH) is a projective radiographic technique, producing radiographic images of the skull or of other anatomical areas from different projections, with minimum magnification and geometrical distortion. Usually two perspectives are represented, latero-lateral and antero-columnerior.

On the market hybrid apparatuses are available, which acquire both panoramic images (2D) and volumetric images (3D)

It is worth noting that teleradiographies, also called cephalometries, can be obtained in two ways:

A direct way, making use of a teleradiographic or hybrid apparatus having a CEPH arm capable of setting patient's head and X-ray sensor at a suitable distance from X-ray source (distance source-detector of about 165 cm);

An indirect way, making use of a CBCT apparatus. In this case, the acquisition is performed positioning the patient at the habitual distance for a CBCT apparatus (i.e. CEPH arm is not necessary). To use a CBCT apparatus to acquire teleradiographic images, first a normal CBCT acquisition of patient's head has to be performed; then the raw images acquired by the sensor are processed using a suitable algorithm (e.g. Feldkamp) so as to obtain a 3D reconstruction of the volume of interest. The volumetric data are then used to obtain an orthogonal or slightly perspectival projection of patient's head, using the absorption values of the different voxels of the reconstructed volume to recreate the necessary transparencies to obtain a teleradiographic image;

According to the orientation of the projection with respect to patient's head, an antero-columnerior (AP) teleradiography or a latero-lateral (LL) teleradiography can be obtained.

For diagnostic reasons CEPH images have to be acquired using patient positioning devices without bite and without chin rest; furthermore in this case, as the volume to be acquired is much bigger than dental arches only, the patient positioning device should also be radio-transparent.

Teleradiographies allow clinical staff to prepare cephalometric tracings of the skull.

Although in any kind of radiographic acquisition keeping patient's head still is fundamental in order to prevent movement artefacts, positioning devices vary because the requirements connected to the positioning itself vary. In particular, when performing a panoramic or a CBCT acquisition, e.g. for orthodontic of implant applications, customarily the patient keeps a bite between her/his incisors, so that they are not overlapping, and radiographs can be used for diagnosis. On the other hand, when performing teleradiographies, the position of incisors, and in general occlusion, must be natural and therefore cephalostats are not provided with a bite and a chin rest.

To obtain a good diagnosis, the head should have ear canals and the intersection of the frontal bone and two nasal bones, called nasion, aligned through radio-opaque markers, which are part of the cephalostat, so as to highlight anatomic anomalies or incorrect positioning of the patient.

In particular, nasion is defined as "The craniometric point at the bridge of the nose where the frontal and nasal bones of the skull meet."

Cephalostats, i.e. the devices for positioning and alignment, in most cases comprise a moving system of two radio-transparent, lateral shafts supporting earpieces and markers, and a front shaft leaning against patient's nasion.

Commonly cephalostats having the moving mechanism (opening and closing of shaft and nasion) supported from top are used, but anyway the cephalostat lays outside of the X-ray bundle, so that the X-ray bundle does not impinge on metallic or non-radio-transparent components, preventing the generation of metal artefacts. Such movement is generally manual, and the cephalostat is fixed permanently and integrally to the apparatus; it allows adjusting the patient positioning device to different skull dimensions.

In CBCT tomographs and for conventional orthopantomographs even radio-transparent craniostats for positioning patients are used, which lack the aligning function; they indicatively comprise a chin support, a forehead support, temples support and a bite.

EP0534548B1 of Dentsply describes a cephalostat for extraoral radiographic apparatuses having a support for nasion, which is movable along a vertical axis and pivoting around the same axis, so that patient's head can be brought in the desired position for acquiring radiographic images.

It is worth specifying that known art cephalostats are radio-transparent in their portions in contact with the patient, but have a portion on which X-rays do not impinge, allowing the movement of the portions in contact with the patient, which is generally made of metal and therefore not radio-transparent, and capable of generating metal artefacts.

WO2007134213 to Xoran Technologies describes the possibility of using a CBCT acquisition to identify the points necessary to perform a cephalometric acquisition.

EP534548 discloses a cephalostat which is provided with adjustable ear plugs and a frontal support enabling immobilizing of an upper jaw of a patient without immobilizing its mandible. The ear plugs guarantee a well defined positioning of the patient's jaw with respect to the beam path of an imaging X-ray beam. The frontal support has preferably the shape of a nose support. The cephalostat is interchangeable with a bite or a chin rest on different Xray imaging apparatus.

SUMMARY OF THE INVENTION

Aim of the present invention is providing a cephalostat allowing the acquisition of teleradiographic images, which is more reliable and easier to control, and cheap to produce.

This object is achieved by an apparatus and a method having the features of the independent claims. Advantageous embodiment and refinements are specified in the claims dependent thereon.

In particular, a cephalostat which is radio-transparent in all the parts on which X-rays impinge and removable is described, to be used on a CBCT volumetric radiographic apparatus, on orthopantomographs or on hybrid apparatuses, with the aim of acquiring teleradiographic images. The cephalostat allows to fix and align patient's head to obtain a cephalometric image starting from a volumetric or planar reconstruction, obtaining an extraoral radiographic apparatus without a fixed arm dedicated to cephalostat support, therefore less cumbersome and mechanically complex. This cephalostat is conceived to be interchangeable with a conventional craniostat for CBCT apparatuses, orthopantomographs or hybrid apparatuses, and integrates the movement of the earpiece shafts and of nasion shaft inside the component itself, even if the mechanism is inside the X-ray bundle, being radio-transparent in the components for movement, too.

The cephalostat components being at least one support member supporting a pair of earpieces at the end of two shafts and a small bar for resting against the nasion and optionally mechanisms for displacing the ear pieces one form the other or one against the other and the small bar for resting against the nasion and the x ray beam may have such an aperture that the said component fall at least partially in the x ray beam path.

The cephalostat according to the present invention has important advantages.

A first advantage connected to the volumetric reconstruction technique is obtaining an extraoral radiographic apparatus capable of acquiring teleradiographies (CEPH) markedly less cumbersome than known art apparatuses, in that to acquire teleradiographies the CEPH arm is not necessary anymore. As above hinted, the CEPH arm is at least 165 cm long.

A second advantage is the interchangeability of the present cephalostat with the craniostat, used for other kinds of acquisition (PAN, CBCT). This allows obtaining hybrid apparatuses, i.e. capable of acquiring PAN, CBCT, CEPH images having reduced dimensions and optimized performances.

A third advantage of the present invention is providing dentists with teleradiographic images which are analogous to traditional teleradiographic images, i.e. obtained through the direct method, while instead they were acquired through the indirect method. The presence of the customary radio-opaque markers (nasion and earpieces) is a help for tracking the cephalometric tracing.

BRIEF DESCRIPTION OF THE DRAWINGS

Further advantages and properties of the present invention are disclosed in the following description, in which exemplary embodiments of the present invention are explained in detail based on the drawings:

FIGS. 3a-3c are front views of extraoral radiographic apparatuses according to the prior art;

FIGS. 7a and 7b are front views of the same extraoral radiographic apparatus, alternatively supporting a craniostat or a cephalostat according to the present invention;

DETAILED DESCRIPTION OF EMBODIMENTS OF THE INVENTION

Figure 1:
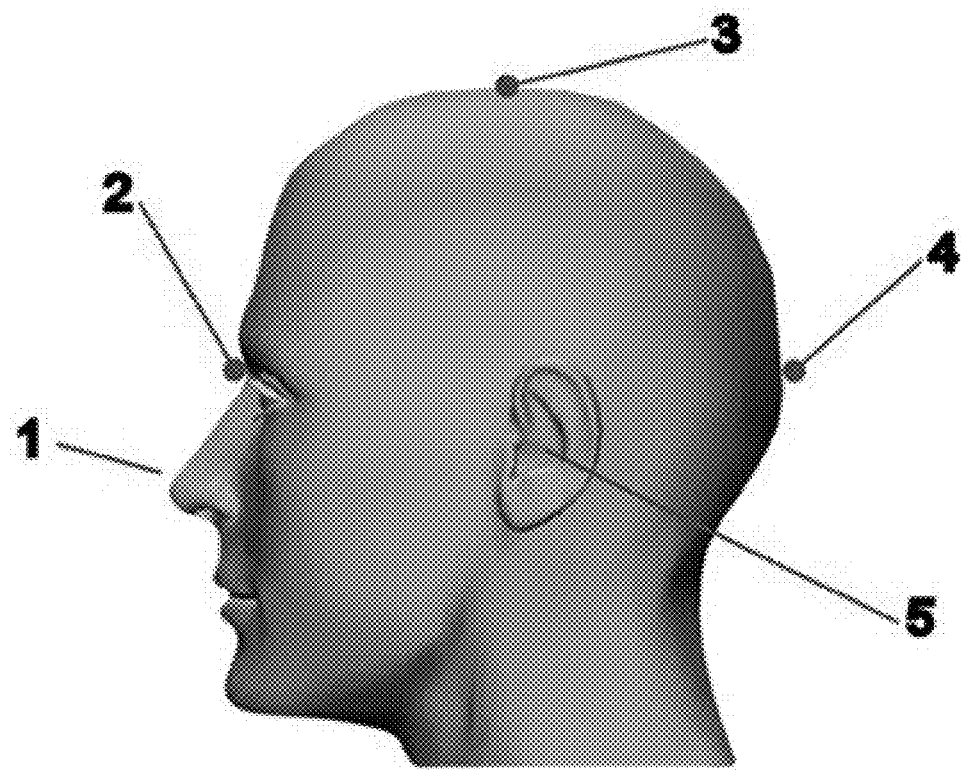
FIG. 1 is an image of a patient's profile, showing the fundamental points for patient's positioning.

FIG. 1 shows the profile of a patient, wherein the fundamental points for patient positioning are highlighted: nose 1, nasion 2, head vertex 3, the columnnerior part or inion 4, ear canal 5.

A cephalometric analysis is performed on a latero-lateral teleradiography; on the image specific bone points are individuated, and, according to their distances and to the angles describing the planes passing through them, facial growth, occlusion and other parameters are studied. Cephalometry allows classifying the skeletal kind of malocclusion, both in the sagittal and in the vertical direction.

Figure 2:
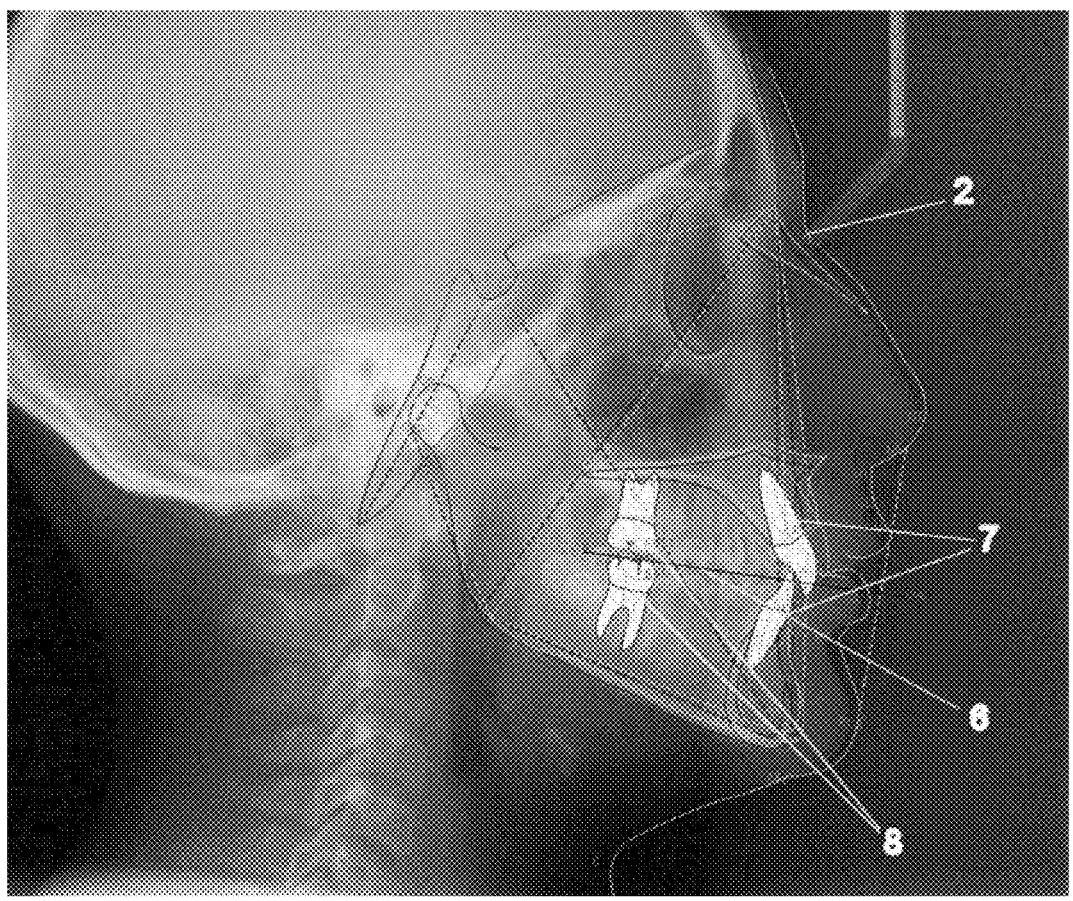
FIG. 2 is a latero-lateral teleradiography, provided with cephalometric tracing.

FIG. 2 shows a latero-lateral teleradiography, on which a cephalometric tracing (dotted lines) was successively superimposed. In the radiograph nasion 2, upper and lower dental arches 6, upper and lower incisors 7, upper and lower molar teeth 8 are shown.

FIGS. 3a-3c shows three examples of extraoral radiographic apparatuses according to the prior art. There are shown: a hybrid device 31 with cephalostat 35 and a dedicated cephalometric arm 34 fixed to column 30, and a craniostat provided with bite 38; a panoramic apparatus 32 with a craniostat 36, provided with a bite 38, integral to the pivoting part, fixed from top; a panoramic apparatus 33 with an integral craniostat 37, provided with bite 38, fixed from the bottom, i.e. fixed on column 30.

From this Figure, one can appreciate what was explained above: the presence of the cephalometric arm leads to much more cumbersome extraoral radiographic apparatuses.

As can be easily appreciated from FIG. 3, typically craniostats can be fixed to the extraoral apparatus from the top, like in apparatuses 31 and 32, of from the bottom, like in the apparatus 33.

Figure 4:
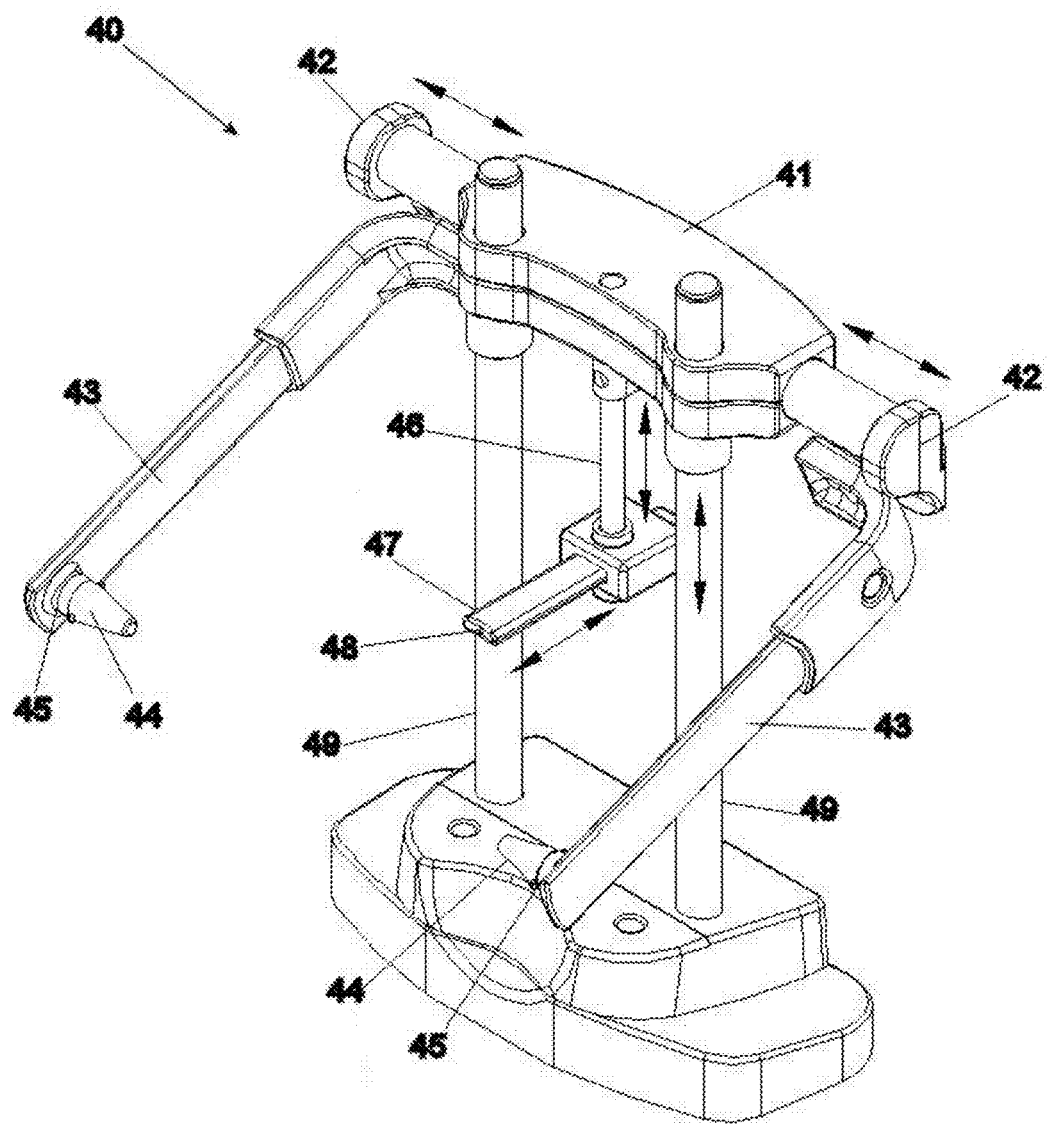
FIG. 4 is an axonometric view of the cephalostat according to the present invention.

FIG. 4 shows the cephalostat 40 according to the present invention, realized in radio-transparent materials like e.g. carbon fibre composite materials, or radio-transparent plastics like polyethylene, or polyurethane or acetal resins or polycarbonate.

The cephalostat 40 comprises a supporting element 41, vertically adjustable in the direction indicated by the double arrow, allowing to move at the same time (opening or closing) a pair of bars 42, supporting a couple of shafts 43 in their turn supporting earpieces 44. The pair of shafts 43 can be moved in the horizontal direction indicated by the double arrow, so as to adjust the position of the shafts themselves to the real dimension of patient's head. Said earpieces 44 have a pair of radio-opaque markers 45, having the aim of marking the position and the alignment of the external ear canal of the patient.

The supporting element 41 allows to move at the same time a small shaft 46 supporting a small bar 47, which can be approached or distanced to/from patient's nasion, in the direction showed by the double arrow. Said small bar 47 supports in its turn a radio-opaque marker 48 capable of radiologically marking the position and the alignment of patient's nasion 2.

The supporting element 41 allows to move all the cephalostat upwards and downwards, through a pair of bars 49. All the movements are provided with friction devices, so as to allow a fluid sliding, but at the same time reduced backlash, in order to guarantee a good structural stiffness.

Figure 5:
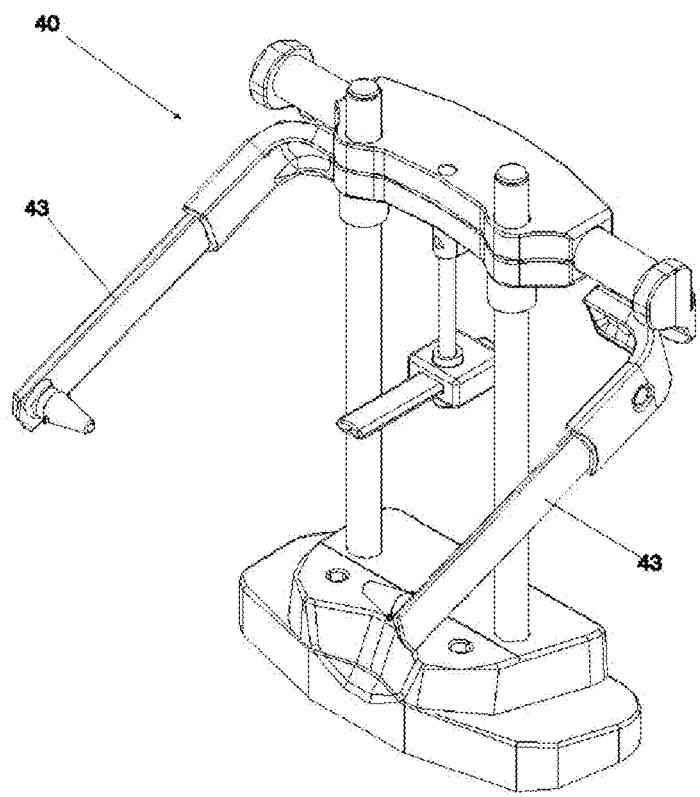
FIG. 5 is an axonometric view of the cephalostat in its position of maximal opening of the earpiece shafts.
Figure 6:
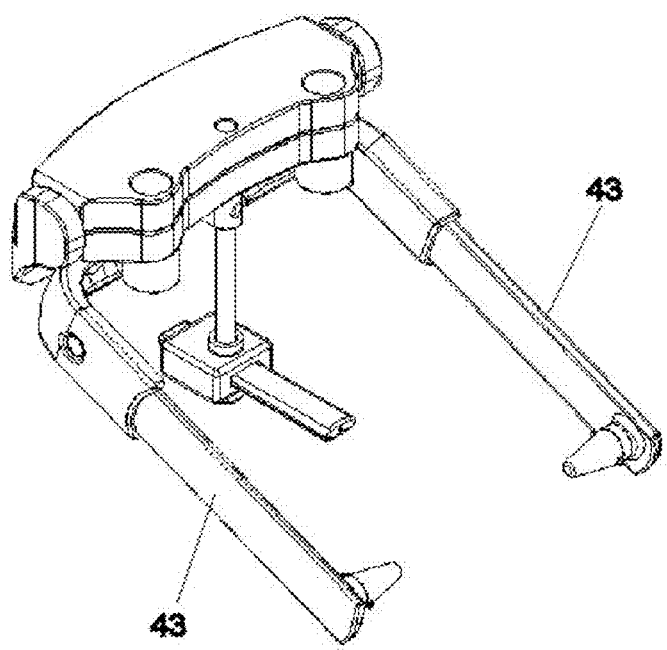
FIG. 6 is an axonometric view of the cephalostat in its position of minimal opening of the earpiece shafts.

FIG. 5 and FIG. 6 allow to appreciate the different adjusting positions of earpiece shafts 43: FIG. 5 shows their position of maximal opening, while FIG. 6 shows their position of maximal closing. Indicatively, latero-lateral skull diameter can range from 9.5 cm to 16.5 cm.

FIGS. 7a and 7b shows the same apparatus 71 according to the present invention, allowing to fix on column 74 a craniostat 72 provided with a bite 73 and chin rest, or a cephalostat 40, according to the kind of radiograph to be acquired. As usual, the apparatus 71 is provided with a C-arm 75 on whose ends an X-ray source and detector are fixed. The C-arm 75 vertically slides with respect to the column 74, so as to adjust its position according to the stature of the specific (not shown) patient.

According to an embodiment of the present invention, the cephalostat comprises a foot on which a structure stands, bearing a couple of earpieces on the end of shaft pair, the small bar for nasion 2 support, and the manual mechanism for adjusting the relative position of said components, in order to adapt them to the head of the single patient under examination. Said base has removable coupling means to a fixing seat on a structural part of an apparatus for acquiring radiographic images of a patient's head or part of it.

In combination with a cephalostat a craniostat can be provided. According to the present invention the craniostat, too, has a fixing base for a fixing seat on a structural part of an apparatus for acquiring radiographic images of a patient's head or part of it.

Advantageously, on the apparatus for acquiring radiographic images there is provided a fixing seat only, for the alternative fixing of the cephalostat or of the craniostat. In this case, the fixing bases of craniostat and cephalostat are both provided with a fixing mechanism, configured so that it can cooperate with the same fixing organs of said unique seat for fixing.

In the illustrated embodiment, the foot comprises a base 80 from which three pins 81, 82, 83 protrude, allowing its removable fixing to a fixing seat on the column (74) of the apparatus, e.g. in the form of a shelf protruding from the column.

Figure 8:
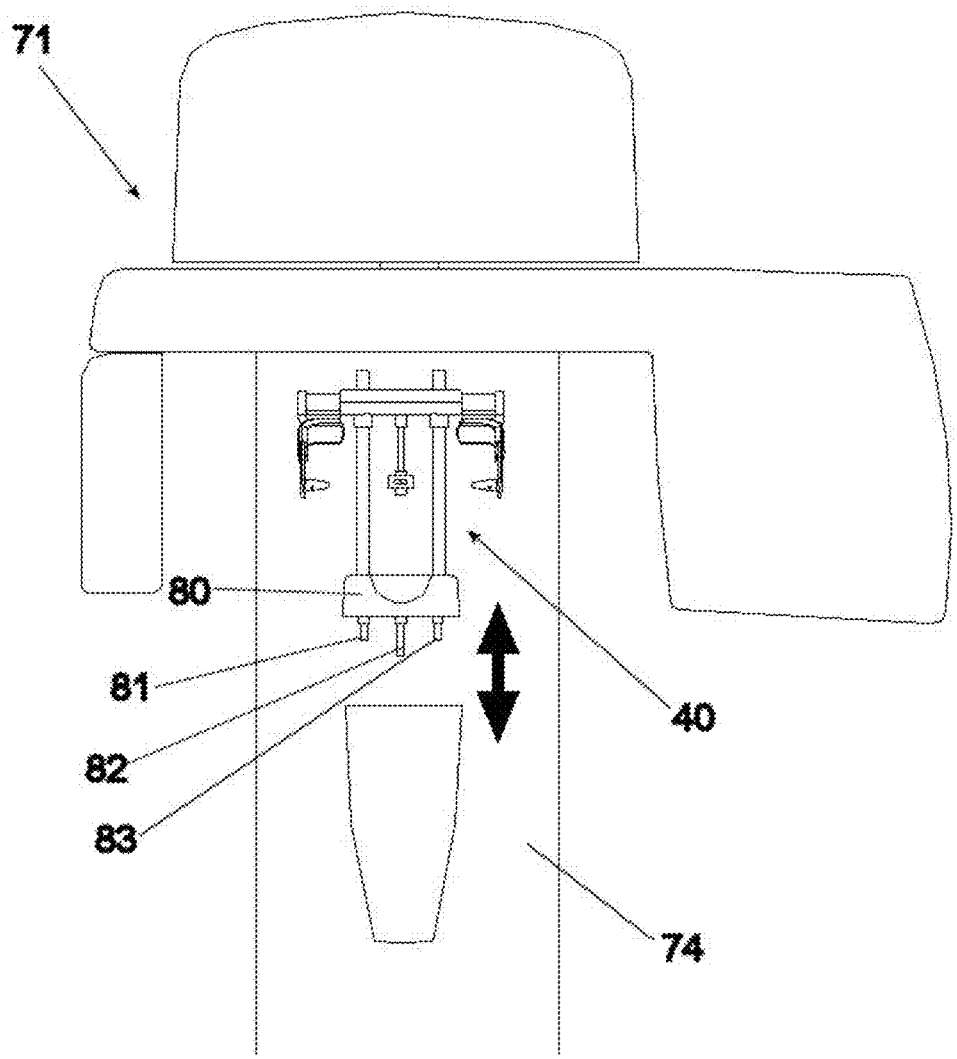
FIG. 8 is a front view of the extraoral radiographic apparatus showing a detail of the fixing of the cephalostat on the column of the apparatus itself.

FIG. 8 shows a detailed embodiment, wherein the cephalostat 40 can easily be fixed and removed to the column 74 of apparatus 71. The cephalostat 40 is provided with a base 80 from which three pins 81, 82, 83 protrude. Said pins are inserted in a corresponding (not shown) seat in the column 74, i.e. in a series of holes having diameter, depth and relative position corresponding to that of the pins on the base of the cephalostat. The cephalostat is fixed to the column 74 through the force of gravity. It is apparent that the craniostat 72 is provided with an analogous base and three (not shown) pins. The cephalostat 40 and the craniostat 72 are perfectly interchangeable on their base, and are removed and positioned moving them upwards or downwards, respectively, in the direction indicated by the double arrow.

Figure 9:
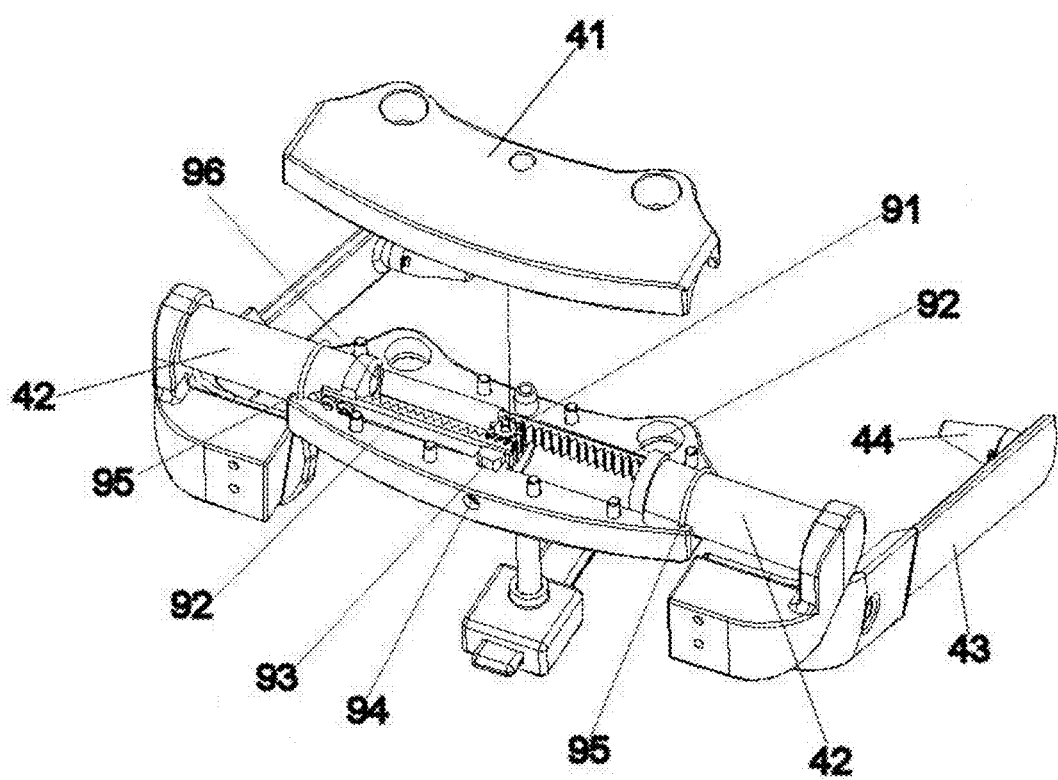
FIG. 9 is an exploded view of the moving mechanism of the earpiece shaft.

FIG. 9 shows an exploded view of the moving mechanism of earpiece shafts 43. The support element 41 is housed in two half-cases containing the mechanism. In this view, the upper half-case is shifted to show the internal mechanism.

A central idler gear 91 (made of acetal plastic) acts at the same time on two racks 92 (made of acetal plastic), which are integral to bars 42. The bars 42, and therefore earpieces 44, opening and closing move simultaneously, performing the same symmetrical shift with respect to the central axis of the device. In the bars 42 there are provided two openings 96, so that each rack enters in the bar itself when it is closing, to reduce as much as possible the encumbrance, and therefor limit the radiologic impact.

A small block 93 (made of acetal plastic) works as a presser through a regulating plastic screw 94, thrusting in a measured way on the system rack/idler gear, so as to reduce plays and pre-load the mechanism.

Two elastic rings 95 (O-ring type) placed at the two ends work through friction on the bars 42 so as to generate a fluid movement.

Figure 10:
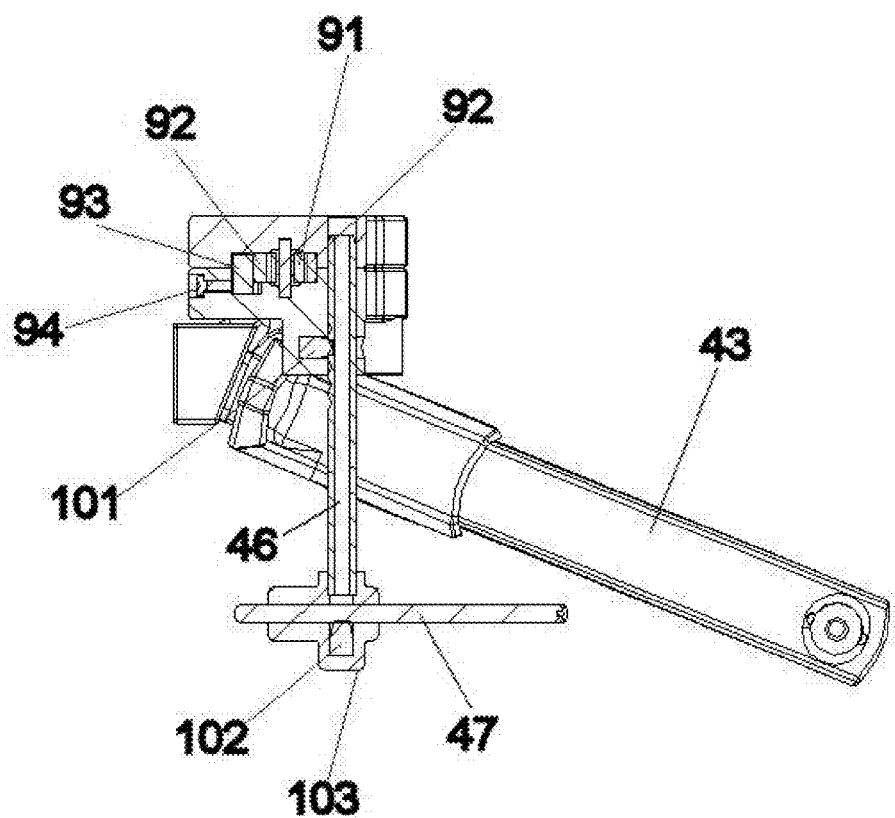
FIG. 10 is a vertical section of the moving mechanism of the nasion support.

FIG. 10 shows the moving mechanism of the nasion support 47, in a section view along the median vertical plan of the device. The movement of the support 47 is double, in that an adjustment with respect both to the vertical axis and to the sagittal axis is needed.

For the vertical adjustment, on the small shaft 46 (made of carbon) a buffer 101 (made of polyurethane) rests, applying a steady pressure so as to perform a friction on the vertical movement of the small shaft itself and to prevent that the small shafts slips out through gravity from its seat. The buffer 101 is freely mounted in a hole of the lower half-case of support element 41. On the small shaft 46 there are provided notches allowing to define pre-set positions, in order to help the human operator to find the most appropriate height.

For the sagittal adjustment, on the small bar 47 (made of polycarbonate) rests an analogous buffer 102 (in polyurethane) exerting a steady pressure, so as to perform friction on the sagittal movement. The buffer is freely mounted in a opening 103 obtained in the support of small bar.

The use of the quoted radio-transparent materials (polyurethane, acetal plastic, carbon) conditioned the design of movement mechanisms, which had the requirement to be of reduced dimensions and sufficiently stiff to guarantee a good patient positioning.

The method for positioning a patient is performed by a human operator who takes care of all the adjustment steps hereunder described, and comprises the following steps:

The (not shown) human operator positions the cephalostat 40 in its seat on the column 74 thanks to the presence of the three pins 81, 82, 83; its position is fixed through the force of gravity;

The human operator first adjusts the apparatus 71 bringing the C-arm 75 at the correct height for the specific (not shown) patient;

The patient approaches to the cephalostat 40 and the human operator adjusts the height position of the supporting element 41 sliding it in the vertical direction on bars 49;

The human operator adjusts the position of the earpiece shafts 43 in width moving the bars 42, so as to insert the earpieces 44 inside the ear canals 5 of the patient The human operator rests the small bar 47 to patient's nasion 2, adjusting its position both in height, sliding it on the small shaft 46, and on the sagittal plane, adjusting its length in the antero-columnerior direction;

Finally, the human operator verifies the correct positioning of the patient thanks to the presence of (not shown) laser markers tracking lines on patient's face, and to the presence of radio-opaque markers 45 and 48 which allow to verify the correct positioning on scout radiographies.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

LIST OF REFERENCE NUMBERS 1 nose
2 nasion
3 vertex
4 inion
5 external ear canal
6 dental arches
7 incisor teeth
8 molar teeth
30 column
31 extraoral radiographic apparatus with CEPH arm
32 extraoral radiographic apparatus
33 extraoral radiographic apparatus
34 cephalometric arm
35 known art cephalostat
36 known art craniostat
37 known art craniostat
38 bite
40 cephalostat according to the present invention
41 supporting element
42 bar
43 earpiece shaft
44 earpiece
45 radio-opaque marker
46 small shaft
47 small bar
48 radio-opaque marker
49 bar
71 extraoral radiographic apparatus
72 craniostat
73 bite
74 column
80 base of the cephalostat
81, 82, 83 pins
91 idler gear
92 rack
93 small block
94 screw
95 O-ring
96 opening
101 buffer
102 buffer
103 opening

The invention claimed is:

1. A cephalostat for acquiring teleradiographic images comprising:
an extraoral radiographic apparatus; and
a plurality of components comprising,
a supporting element for a pair of earpieces provided at ends of two shafts; and
a bar for resting again a nasion,
wherein said components are manually adjustable in relation to a skull of a patient under examination, said components falling at least partially inside a path of an imaging x-ray beam,
wherein said cephalostat is free from metallic parts at least in parts of said components falling inside the X-ray beams path, with exception of radio-opaque markers, and
wherein said cephalostat is interchangeable with a craniostat fixed in a same apparatus seat,
further comprising a base from which a plurality of pins protrude, thereby enabling a removable fixing of the based to a column of extraoral radiographic apparatus.

2. The cephalostat according to claim 1, wherein said cephalostat is configured to acquire teleradiographic images without a dedicated CEPH arm.

3. The cephalostat according to claim 1, further comprising a base, on which a structure stands, bearing said pair of earpieces on the ends of the two shafts, said bar for resting the nasion, and a manual mechanism for adjusting a relative position of said components, such to adapt said components to a head of the patient under examination, said base having a removable coupling system to a fixing seat on a structural part of an apparatus for acquiring radiographic images of the patient's head or part of it.

4. The cephalostat according to claim 3, wherein in combination with the craniostat having a fixing foot to the fixing seat, for an alternative fixing of the cephalostat or of the craniostat to the apparatus for acquiring radiographic images, fixing bases of the craniostat and the cephalostat are both provided with a fixing mechanism, configured to cooperate with the coupling system to the fixing seat.

5. The cephalostat according to claim 1, further comprising a radio-transparent mechanism moving the earpiece shafts.

6. The cephalostat according to claim 1, wherein two radio-opaque markers are fixed on the pair of earpieces, and wherein a radio-opaque marker is fixed at the end of the bar in contact with nasion.

7. The cephalostat according to claim 1, wherein said cephalostat is provided within an extraoral radiographic apparatus configured to acquire CBCT or panoramic images.

8. A cephalostat for acquiring teleradiographic images comprising:
an extraoral radiographic apparatus; and
a plurality of components comprising,
a supporting element for a pair of earpieces provided at ends of two shafts; and
a bar for resting again a nasion,
wherein said components are manually adjustable in relation to a skull of a patient under examination, said components falling at least partially inside a path of an imaging x-ray beam,
wherein said cephalostat is free from metallic parts at least in parts of said components falling inside the X-ray beams path, with exception of radio-opaque markers, and
wherein said cephalostat is interchangeable with a craniostat fixed in a same apparatus seat,
further comprising a radio-transparent mechanism moving the earpiece shafts, wherein said radio-transparent mechanism has friction devices for manually moving said components.

9. A method of positioning a patient for acquisition of cranial teleradiographies with a cephalostat according to claim 1, comprising the following steps:
- manually positioning the cephalostat in a corresponding seat provided on an apparatus for acquiring radiographic images and coupling a foot of said cephalostat to said seat;
- manually performing a first adjustment of the apparatus bringing a C-arm at a height suitable for the patient;
- positioning the patient near to the cephalostat and manual adjusting a height position of a supporting element by sliding said supporting element vertically on first bars;
- adjusting a width position of earpiece shafts working on second bars so as to insert earpieces and position radio-opaque markers inside the patient's external ear canals; and
- positioning a third bar leaning with the radio-opaque marker against the patient's nasion, adjusting a position of the third bar both in height, sliding the third bar on a shaft, and on a sagittal plane, adjusting a length of the third bar in an antero-posterior direction.

10. A method of positioning a patient making use of a cephalostat for acquiring teleradiographic images comprising:
- an extraoral radiographic apparatus; and
- a plurality of components comprising,
  - a supporting element for a pair of earpieces provided at ends of two shafts; and
  - a bar for resting again a nasion,
- wherein said components are manually adjustable in relation to a skull of a patient under examination, said components falling at least partially inside a path of an imaging x-ray beam,
- wherein said cephalostat is free from metallic parts at least in parts of said components falling inside the X-ray beams path, with exception of radio-opaque markers,
- wherein said cephalostat is interchangeable with a craniostat fixed in a same apparatus seat, and
- wherein two radio-opaque markers are fixed on the pair of earpieces, and wherein a radio-opaque marker is fixed at the end of the bar in contact with nasion, the method comprising:
- verifying a correct positioning of the patient through presence of laser rays tracking lines on the patient's face and of radio-opaque markers, thereby enabling a verification of correct positioning on scout radiographies.

* * * * *